(12) United States Patent
Kettlewell et al.

(10) Patent No.: US 8,133,504 B2
(45) Date of Patent: Mar. 13, 2012

(54) TISSUE-ADHESIVE MATERIALS

(75) Inventors: Graeme Kettlewell, Bradford (GB);
David John Mandley, Selby (GB);
David Harry Fortune, Harrogate (GB);
Ian Thompson, Bradford (GB); Diane Morris, Huddersfield (GB)

(73) Assignee: Tissuemed Limited, Leeds (GB)

( * ) Notice: Subject to any disclaimer, the term of this patent is extended or adjusted under 35 U.S.C. 154(b) by 1258 days.

(21) Appl. No.: 11/572,976

(22) PCT Filed: Jul. 29, 2005

(86) PCT No.: PCT/GB2005/002981
§ 371 (c)(1),
(2), (4) Date: Jan. 30, 2007

(87) PCT Pub. No.: WO2006/013337
PCT Pub. Date: Feb. 9, 2006

(65) Prior Publication Data
US 2007/0286891 A1  Dec. 13, 2007

(30) Foreign Application Priority Data

Aug. 3, 2004 (GB) .................................. 0417267.2
Jan. 18, 2005 (EP) .................................. 05075123

(51) Int. Cl.
*A61L 15/58* (2006.01)
*C08F 26/10* (2006.01)
(52) U.S. Cl. ...................... 424/443; 526/238.1; 526/264
(58) Field of Classification Search ........................ None
See application file for complete search history.

(56) References Cited

U.S. PATENT DOCUMENTS

| | | | |
|---|---|---|---|
| 4,179,337 A | 12/1979 | Davis et al. | |
| 4,453,939 A | 6/1984 | Zimmerman et al. | |
| 4,456,711 A | 6/1984 | Pietsch et al. | |
| 4,503,034 A | 3/1985 | Maupetit et al. | |
| 4,744,364 A | 5/1988 | Kensey | |
| 4,804,691 A | 2/1989 | English et al. | |
| 4,837,379 A | 6/1989 | Weinberg | |
| 4,911,926 A | 3/1990 | Henry et al. | |
| 4,913,903 A | 4/1990 | Sudmann et al. | |
| 4,940,737 A | 7/1990 | Braatz et al. | |
| 5,017,229 A | 5/1991 | Burns et al. | |
| 5,066,521 A | 11/1991 | Morsy et al. | |
| 5,066,709 A | 11/1991 | Chaudhuri et al. | |
| 5,122,614 A | 6/1992 | Zalipsky | |
| 5,135,751 A | 8/1992 | Henry et al. | |
| 5,162,430 A | 11/1992 | Rhee et al. | |
| 5,209,776 A | 5/1993 | Bass et al. | |
| 5,292,362 A | 3/1994 | Bass et al. | |
| 5,304,595 A | 4/1994 | Rhee et al. | |
| 5,306,504 A | 4/1994 | Lorenz | |
| 5,312,435 A | 5/1994 | Nash et al. | |
| 5,324,775 A | 6/1994 | Rhee et al. | |
| 5,328,955 A | 7/1994 | Rhee et al. | |
| 5,334,640 A | 8/1994 | Desai et al. | |
| 5,410,016 A | 4/1995 | Hubbell et al. | |
| 5,462,990 A | 10/1995 | Hubbell et al. | |
| 5,468,811 A | 11/1995 | Moro et al. | |
| 5,514,379 A | 5/1996 | Weissleder et al. | |
| 5,527,856 A | 6/1996 | Rhee et al. | |
| 5,571,181 A | 11/1996 | Li | |
| 5,575,815 A | 11/1996 | Slepian et al. | |
| 5,580,923 A | 12/1996 | Yeung et al. | |
| 5,583,114 A | 12/1996 | Barrows et al. | |
| 5,614,587 A | 3/1997 | Rhee et al. | |
| 5,629,384 A * | 5/1997 | Veronese et al. | ........... 525/326.8 |
| 5,643,464 A | 7/1997 | Rhee et al. | |
| 5,752,974 A | 5/1998 | Rhee et al. | |
| 5,770,229 A | 6/1998 | Tanihara et al. | |
| 5,786,421 A | 7/1998 | Rhee et al. | |
| 5,791,352 A | 8/1998 | Reich et al. | |
| 5,863,662 A | 1/1999 | Hornby et al. | |
| 5,874,500 A | 2/1999 | Rhee et al. | |
| 5,931,165 A | 8/1999 | Reich et al. | |
| 5,989,215 A | 11/1999 | Delmotte et al. | |
| 6,007,544 A | 12/1999 | Kim | |
| 6,051,648 A | 4/2000 | Rhee et al. | |
| 6,063,061 A | 5/2000 | Wallace et al. | |

(Continued)

FOREIGN PATENT DOCUMENTS

CA    2 363 916 A1    7/2000

(Continued)

OTHER PUBLICATIONS

Machine translation of DE 3502998; Muller-Schulte. Jan. 30, 1985.*
Israelachvili, Jacob, "The Different Faces of Poly(Ethylene Glycol)," Proc. Natl. Acad. Sci. 94:8378-8379 (1997).
Don et al., "Studies on the Degradation Behavior of Chitosan-g-Poly (Acrylic Acid) Copolymers," Tamkang J. of Science and Engineering 5(4):235-240 (2002).
Birch et al., "Methylene Blue Based Protein Solder for Vascular Anastomoses: An In Vitro Burst Pressure Study," *Lasers in Surgery and Medicine* 26:323-329 (2000).
Delgado et al., "The Uses and Properties of PEG-Linked Proteins," *Critical Reviews in Therapeutic Drug Carrier Systems* 9(3,4):249-304 (1992).

(Continued)

*Primary Examiner* — Shanon A Foley
(74) *Attorney, Agent, or Firm* — LeClairRyan, a Professional Corporation

(57) ABSTRACT

This invention related to a tissue-adhesive sheet comprising a homogeneous, preformed and cross-linked matrix formed from one or more polymers, and having at least one surface that, in use, is exposed, at least one of said one or more polymers being a synthetic polymer and having appendant functional groups of a first form, cross-linking of said matrix being via a proportion of said functional groups of the first form, and the remainder of said functional groups of the first form being free. The sheet is particularly useful as a tissue adhesive and sealant, and is intended for topical application to internal and external surfaces of the body for therapeutic reasons. The invention further relates to sheets comprising a scaffold material, three-dimensional articles formed from similar material to that of the sheet and to implantable medical devices coated with such material.

19 Claims, 4 Drawing Sheets

U.S. PATENT DOCUMENTS

| | | | |
|---|---|---|---|
| 6,066,325 A | 5/2000 | Wallace et al. | |
| 6,075,107 A | 6/2000 | Kothrade et al. | |
| 6,166,130 A | 12/2000 | Rhee et al. | |
| 6,264,702 B1 | 7/2001 | Ory et al. | |
| 6,312,725 B1 | 11/2001 | Wallace et al. | |
| 6,323,278 B2 | 11/2001 | Rhee et al. | |
| 6,329,115 B1 | 12/2001 | Yamashita | |
| 6,379,373 B1 | 4/2002 | Sawhney et al. | |
| 6,387,978 B2 | 5/2002 | Ronan et al. | |
| 6,391,049 B1 | 5/2002 | McNally et al. | |
| 6,458,889 B1 | 10/2002 | Trollsas et al. | |
| 6,495,127 B1 | 12/2002 | Wallace et al. | |
| 6,534,591 B2 | 3/2003 | Rhee et al. | |
| 6,548,729 B1 | 4/2003 | Seelich et al. | |
| 6,566,406 B1 | 5/2003 | Pathak et al. | |
| 6,624,245 B2 | 9/2003 | Wallace et al. | |
| 6,649,162 B1 | 11/2003 | Biering et al. | |
| 6,664,331 B2 | 12/2003 | Harris et al. | |
| 6,673,093 B1 | 1/2004 | Sawhney | |
| 6,676,962 B1 | 1/2004 | Muller | |
| 6,689,148 B2 | 2/2004 | Sawhney et al. | |
| 6,703,047 B2 | 3/2004 | Sawhney et al. | |
| 6,733,774 B2 | 5/2004 | Stimmeder | |
| 6,800,671 B1 | 10/2004 | Montgomery et al. | |
| 6,818,018 B1 | 11/2004 | Sawhney | |
| 6,833,408 B2 | 12/2004 | Sehl et al. | |
| 6,869,938 B1 | 3/2005 | Schwartz et al. | |
| 6,875,796 B2 | 4/2005 | Stedronsky | |
| 6,887,974 B2 | 5/2005 | Pathak | |
| 6,894,140 B2 | 5/2005 | Roby | |
| 6,916,909 B1 | 7/2005 | Nicolas et al. | |
| 6,921,412 B1 | 7/2005 | Black et al. | |
| 6,923,961 B2 | 8/2005 | Liu et al. | |
| RE38,827 E | 10/2005 | Barrows et al. | |
| 6,989,192 B2 | 1/2006 | Huseman et al. | |
| 7,009,034 B2 | 3/2006 | Pathak et al. | |
| 7,057,019 B2 | 6/2006 | Pathak | |
| 7,727,547 B2 * | 6/2010 | Fortune et al. | 424/445 |
| 2002/0013408 A1 | 1/2002 | Rhee et al. | |
| 2002/0042473 A1 | 4/2002 | Trollsas et al. | |
| 2002/0106409 A1 | 8/2002 | Sawhney et al. | |
| 2002/0114775 A1 | 8/2002 | Pathak | |
| 2002/0165337 A1 | 11/2002 | Wallace et al. | |
| 2003/0119985 A1 | 6/2003 | Sehl et al. | |
| 2003/0133967 A1 | 7/2003 | Ruszczak et al. | |
| 2003/0149173 A1 | 8/2003 | Rhee et al. | |
| 2004/0102797 A1 | 5/2004 | Golden et al. | |
| 2004/0121951 A1 | 6/2004 | Rhee | |
| 2004/0131554 A1 | 7/2004 | Rowe et al. | |
| 2004/0138329 A1 | 7/2004 | Hubbell et al. | |
| 2004/0191277 A1 | 9/2004 | Sawhney et al. | |
| 2004/0234574 A9 | 11/2004 | Sawhney et al. | |
| 2004/0235708 A1 | 11/2004 | Rhee et al. | |
| 2004/0242770 A1 * | 12/2004 | Feldstein et al. | 525/54.3 |
| 2004/0247691 A1 | 12/2004 | Marx et al. | |
| 2005/0002893 A1 | 1/2005 | Goldmann | |
| 2005/0003012 A1 | 1/2005 | Woller et al. | |
| 2005/0004599 A1 | 1/2005 | McNally-Heintzelman et al. | |
| 2005/0008632 A1 | 1/2005 | Stimmeder | |
| 2005/0010239 A1 | 1/2005 | Chefitz | |
| 2005/0015036 A1 | 1/2005 | Lutri et al. | |
| 2005/0069589 A1 | 3/2005 | Lowinger et al. | |
| 2005/0074495 A1 | 4/2005 | Schwartz et al. | |
| 2005/0085605 A1 | 4/2005 | Nathan | |
| 2005/0096388 A1 | 5/2005 | Hunter et al. | |
| 2005/0107578 A1 | 5/2005 | Williams et al. | |
| 2005/0125012 A1 | 6/2005 | Houser et al. | |
| 2005/0129733 A1 | 6/2005 | Milbocker et al. | |
| 2005/0154125 A1 | 7/2005 | Rhee | |
| 2005/0208095 A1 | 9/2005 | Hunter et al. | |
| 2005/0215748 A1 | 9/2005 | Milbocker | |
| 2005/0228433 A1 | 10/2005 | Bucay-Couto et al. | |
| 2005/0281866 A1 | 12/2005 | Jarrett et al. | |
| 2006/0147409 A1 | 7/2006 | Pathak et al. | |
| 2009/0044895 A1 | 2/2009 | Kettlewell et al. | |
| 2010/0233246 A1 | 9/2010 | Sehl et al. | |

FOREIGN PATENT DOCUMENTS

| | | |
|---|---|---|
| DE | 3502998 | 7/1986 |
| DE | 259 351 A | 8/1988 |
| DE | 198 59 611 A1 | 6/2000 |
| EP | 0 099 758 A2 | 2/1984 |
| EP | 0 226 264 A1 | 6/1987 |
| EP | 0 732 109 A1 | 9/1996 |
| EP | 0 846 477 A1 | 6/1998 |
| EP | 0 930 074 A1 | 7/1999 |
| EP | 1 003 571 B1 | 5/2000 |
| EP | 1 216 717 A1 | 6/2002 |
| EP | 1 216 718 A1 | 6/2002 |
| JP | 2003-026726 | 1/2003 |
| WO | WO 92/02238 | 2/1992 |
| WO | WO 92/14513 | 9/1992 |
| WO | WO 94/21306 | 9/1994 |
| WO | WO 96/22054 | 7/1996 |
| WO | WO 96/22797 | 8/1996 |
| WO | WO 96/31237 | 10/1996 |
| WO | WO 97/17025 | 5/1997 |
| WO | WO 97/22371 | 6/1997 |
| WO | WO 97/29715 | 8/1997 |
| WO | WO 98/16165 | 4/1998 |
| WO | 9832474 A1 | 7/1998 |
| WO | WO 98/48716 | 11/1998 |
| WO | 99/15210 A2 | 4/1999 |
| WO | WO 99/52481 | 10/1999 |
| WO | WO 00/02539 | 1/2000 |
| WO | 00/02359 A2 | 2/2000 |
| WO | WO 00/10618 | 3/2000 |
| WO | WO 00/38752 | 7/2000 |
| WO | WO 00/59380 A3 | 10/2000 |
| WO | 01/30405 A1 | 5/2001 |
| WO | WO 01/30405 | 5/2001 |
| WO | WO 01/30410 | 5/2001 |
| WO | WO 01/56475 | 8/2001 |
| WO | WO 01/58452 | 8/2001 |
| WO | WO 02/09792 A1 | 2/2002 |
| WO | 02/034304 A1 | 5/2002 |
| WO | WO 02/058749 A2 | 8/2002 |
| WO | 03/020824 A2 | 3/2003 |
| WO | 03094898 A2 | 11/2003 |
| WO | 2004060405 A2 | 7/2004 |
| WO | 2004/087227 A1 | 10/2004 |
| WO | 2004108179 A1 | 12/2004 |
| WO | 2005055958 A2 | 6/2005 |
| WO | 2005089659 A1 | 9/2005 |
| WO | 2007088402 | 9/2007 |

OTHER PUBLICATIONS

Duval et al., "Synthesis and Characterization of Some Covalent Dextran-Polyoxyethyleneglycol Derivatives," *Carbohydrate Polymers* 15:233-242 (1991).

Erout et al., "Radical-Initiated Copolymers of N-vinyl Pyrrolidone and N-Acryloxy Succinimide: Kinetic and Microstructure Studies," *Polymer* 37(7):1157-1165 (1996).

Harris et al., "Synthesis and Characterization of Poly(ethylene Glycol) Derivatives," *J. Polymer Sci.* 22:341-352 (1984).

Mandley et al., "Photon Activated Biological Adhesives in Surgery," *International Journal of Adhesion & Adhesives* 20:97-102 (2000).

Nishi & Kotaka, "Complex-Forming Poly (oxyethylene):Poly(acrylic acid) Interpenetrating Polymer Networks. 1. Preparation, Structure, and Viscoelastic Properties," *Macromolecules* 18(8):1519-1525 (1985).

Sánchez-Chaves et al., "Poly (Vinyl Alcohol) Functionalized by Monosuccinate Groups. Coupling of Bioactive Amino Compounds," *Polymer* 39(13):2751-2757 (1998).

Zalipsky et al., "Attachment of Drugs to Polyethylene Glycols," *Eur. Polym. J.* 19(12):1177-1183(1983).

Zalipsky et al., "Evaluation of a New Reagent for Covalent Attachment of Polyethylene Glycol to Proteins," *Biotechnology and Applied Biochemistry* 15:100-114 (1992).

Zalipsky et al., "Succinimidyl Carbonates of Polyethylene Glycol: Useful Reactive Polymers for Preparation of Protein Conjugates," *Polymer Reprints*, pp. 173-174 (1990).

Iwata et al., "A Novel Surgical Glue Composed of Gelatin and N-hydroxysuccinimide Activated Poly(L-glutamic acid): Part 1. Synthesis of Activated poly(L-glutamic acid) and its Gelation with Gelatin," *Biomaterials* 19:1869-1876 (1998).

Disley et al., "Covalent Coupling of Immunoglobulin G to a Poly(Vinyl)Alcohol-Poly(Acrylic Acid) Graft Polymer as a Method of Fabricating the Interfacial-Recognition Layer of a Surface Plasmon Resonance Immunosensor," *Biosensors and Bioelectronics* 13(3-4):383-396 (1998) (abstract only).

* cited by examiner

TISSUE-ADHESIVE MATERIALS

This application is a national stage application under 35 U.S.C. 371 of PCT/GB2005/002981, and claims the priority benefit of British Patent Application (GB) 0417267.2, filed Aug. 3, 2004, and European Patent Application (EP) 05075123.9, filed Jan. 18, 2005.

FIELD OF THE INVENTION

This invention relates to a flexible sheet comprising a cross-linked polymer matrix, the sheet being suitable for use as a tissue adhesive and sealant, and intended for topical application to internal and external surfaces of the body, for therapeutic purposes. The invention also relates to a process for the preparation of such a sheet, and to methods of using such a sheet. In particular the invention relates to a self-adhesive, biocompatible and hydratable polymeric sheet, which may be used for therapeutic purposes such as wound healing, joining, sealing and reinforcing weakened tissue, and for drug delivery, and to a process for preparing, and methods of using, such a sheet. The invention further relates to three-dimensional articles formed from similar material to that of the sheet and to implantable medical devices coated with such material.

BACKGROUND OF THE INVENTION

There is considerable interest in the use, for a number of surgical or other therapeutic applications, of materials that adhere to biological tissues, eg as an alternative to the use of mechanical fasteners such as sutures, staples etc. Formulations of such materials that have hitherto been proposed include viscous solutions or gels that are either manufactured in that form or are prepared immediately prior to use by mixing of the ingredients. Such formulations are then applied to the tissue surface using a suitable applicator device such as a syringe.

Formulations of the type described above suffer from a number of disadvantages. If the formulation is of low viscosity, it may spread from the area of application and hence be difficult to apply precisely to the desired area of tissue. If the formulation is more viscous, on the other hand, it may be difficult to dispense. In either case, the formulation, being prepared in hydrated form, may have a limited lifetime and may be subject to premature curing. It may therefore be necessary for the whole of the formulation to be used at once or discarded. Also, the preparation of formulations immediately prior to use by mixing of ingredients is obviously laborious and time-consuming. In addition to these drawbacks, the degree of adhesion between tissue surfaces that is provided by such formulations may be less than would be desired.

Formulations of tissue adhesive materials have also been applied to a suitable support for application to the tissue surface. The use of therapeutic materials in the form of a sheet, patch or film, for topical administration to either internal or external organs of the body, is well documented for a wide range of medical applications. A disadvantage of products proposed hitherto, however, is that the degree of adhesion to the underlying tissue, particularly in the longer term, may be inadequate. While the initial adhesion may be satisfactory, the sheet may subsequently become detached from the tissue, often after only a few seconds or minutes, eg as a result of hydration of the sheet following its application. In addition, the flexibility of the product may be insufficient for it to conform readily to the surface to which it is applied, which may also have an adverse effect on its adhesion.

As a result of the inadequate adhesion of these products, it may be necessary to provide further reinforcement, eg through mechanical attachment using sutures, staples or the like. Alternatively, energy (eg light or heat energy) may be applied in order to initiate chemical bonding of the adhesive formulation to the underlying tissue, and hence bonding of the tissue surfaces to each other. Clearly, such approaches introduce further drawbacks. The use of mechanical fastenings such as sutures or staples is often the very thing that the use of such products is intended to replace or avoid. In many instances, the use of such fastenings is either not wholly effective (eg on the lung) or undesirable, as their introduction gives rise to further areas of tissue weakness. The use of external energy requires the provision and operation of a source of such energy. Such energy sources may be expensive and difficult to operate, particularly in the confines of an operating theatre or similar environment. Also, the use of external energy for attachment can be both time-consuming and (in some cases) requires significant careful judgement on the part of the surgeon, to evaluate when sufficient energy has been delivered to effect attachment without damaging the underlying tissue.

WO 00/02539 discloses a topical plaster with an active agent in the form of a non-steroidal antirheumatic agent. The plaster consists of an inert back layer to which is applied a self-adhesive matrix layer that is based on a polyacrylate adhesive and which contains the active agent.

WO 02/34304 discloses multilamellar sheets for topical application both internally and externally of the body. The sheets comprise cross-linkable material and a synthetic polymer having bioadhesive properties.

WO 2004/087227 discloses tissue-adhesive formulations comprising particulate cross-linkable material in admixture with particulate material comprising tissue-reactive functional groups. The formulations may be applied to a core material in order to form a sheet suitable for application to the body.

WO 03/20824 discloses a self-adhesive polyacrylic acid-based gel matrix that comprises a homopolymer or copolymer of vinyl pyrrolidone as a crosslinker for the polyacrylic acid.

There have now been devised improvements to tissue-adhesive sheets or the like of the general type described above, and to related applications of tissue-adhesive material, that overcome or substantially mitigate the above-mentioned and/or other disadvantages of the prior art.

BRIEF SUMMARY OF THE INVENTION

According to a first aspect of the invention, there is provided a tissue-adhesive sheet comprising a homogeneous, preformed and cross-linked matrix formed from one or more polymers, and having at least one surface that, in use, is exposed, at least one of said one or more polymers being a synthetic polymer and having appendant functional groups of a first form, cross-linking of said matrix being via a proportion of said functional groups of the first form, and the remainder of said functional groups of the first form being free.

In certain embodiments, the functional groups of the first form are the only appendant groups present in the synthetic polymer (or one or more of the synthetic polymers, where the matrix comprises more than one synthetic polymer having functional groups of a first form).

In other embodiments, the synthetic polymer (or one or more of the synthetic polymers, where the matrix comprises more than one synthetic polymer having functional groups of a first form) may further comprise additional appendant groups that are different to the first form of functional group.

In certain embodiments, where the matrix comprises more than one synthetic polymer, the additional appendant groups that are present on the more than one synthetic polymers and that are different to the first form of functional group may all be the same or they may be different, ie the additional appendant groups may be groups of more than one type.

In the invention, a proportion of the functional groups of the first form are involved in cross-linking of the matrix, while the remainder are free. By this is meant simply that some, but only some, of those functional groups react with other functional groups present in the formulation during manufacture so as to form the cross-linked matrix, while the remainder of the functional groups of the first form do not become involved in cross-linking during manufacture and so are present in unreacted form in the finished product. Methods by which it is possible to ensure that only some of the functional groups of the first form become involved in cross-linking of the matrix will be readily apparent to those skilled in the art, one such method involving the mixing of ingredients having appropriate stoichiometries.

The first form of functional group may be any functional group that is capable of reaction with one or more components in the formulation to bring about cross-linking of the matrix.

Cross-linking of the matrix is most preferably by means of covalent bonding.

Preferably, the first form of functional group is such as to confer on the sheet bioadhesive properties. By this is meant that the material should exhibit good initial adhesion to biological tissue to which it is applied. Polymers with such properties typically contain chemical groups with a high ionic density, eg hydroxyl, carboxyl, amide, lactam, ether and ester groups, and salts thereof, which interact cooperatively with tissue, through the formation of ionic and hydrogen bonds, dipole-dipole interactions and Van der Waals forces.

The first form of functional group is therefore preferably selected from the group consisting of hydroxyl, carboxyl, amide, lactam, ether and ester groups. Particularly preferred functional groups of a first form are hydroxyl or carboxyl groups.

Some of the first form of functional groups that are present in the or each synthetic polymer are involved in cross-linking of the matrix. Such cross-linking takes place during manufacture of the sheet, rather than after application of the sheet to tissue (though it is possible that a certain amount of additional cross-linking may then ensue). The remainder of the first form of functional groups are free. In certain embodiments of the invention, at least some of the free functional groups of the first form are in a derivatised or activated form, so as to form tissue-reactive functional groups, ie groups that are chemically reactive towards the tissue to which the sheet is, in use, applied, or which exhibit increased reactivity to tissue. For example, where the first form of functional group is a carboxyl group, a proportion of the free carboxyl groups may be converted to reactive esters, in particular N-hydroxysuccinimide (NHS) ester groups.

In other embodiments of the invention, at least some of the free functional groups of the first form are coupled to additional moieties, eg polymeric moieties, that contain tissue-reactive functional groups.

The sheet according to the invention is advantageous primarily in that it bonds effectively to tissue, enabling it to be used in a variety of medical applications. In preferred embodiments, the sheet exhibits good initial adhesion to the tissue to which it is applied (and may thus be described as "self-adhesive"), and furthermore remains well-adhered to the tissue over a longer timescale. Without wishing to be bound by any theory, it is believed that the initial adhesion of the sheet to the tissue is attributable to electronic bonding of the sheet to the tissue, and this is supplemented or replaced by chemical bonding between the tissue-reactive functional groups of the formulation and the tissue, in particular between amine and/or thiol groups on the tissue surface and the tissue-reactive groups of the sheet.

The sheet exhibits good initial adhesion to the tissue surface, this being believed to be due to Van der Waals forces and/or hydrogen bonding between the sheet and the tissue surface. On contact with the tissue surface the sheet becomes hydrated, thereby causing reaction between the tissue-reactive functional groups and the underlying tissue surface. Such reactions between the tissue-reactive functional groups and the underlying tissue result in high adhesion between the sheet and the tissue surface. The sheet may absorb physiological fluids (as a consequence of application onto exuding tissue surfaces), and any additional solutions used to hydrate the sheet following application (such fluids can be commonly used solutions used in surgical irrigation), becoming more compliant and adherent to the tissue surfaces, and thereby providing an adhesive sealant, haemostatic and pneumostatic function.

The use of the sheet reduces or eliminates the need for additional means of mechanical attachment to the tissue (eg sutures or staples), or the need to provide external energy in the form of heat or light to bring about adherence of the sheet to the underlying tissue. Another advantage of the sheet according to the invention is that it is applied to the tissue as a preformed article, rather than being prepared by mixing of materials immediately prior to use.

In addition, because the sheet is made up in solid form that is, until hydrated upon and following contact with the tissue surface, essentially inactive, the sheet is not prone to premature reaction and as a result its shelf-life may be considerable, eg more than six months when stored appropriately at room temperature.

By the term "sheet" is meant an article with a thickness that is considerably less than its other dimensions. Such an article may alternatively be described as a patch or a film.

Because the preformed and cross-linked matrix is homogeneous, by which is meant that it has a continuous and uniform composition throughout its extent, rather than having a multilamellar structure or being formed of discrete physical domains, eg particles, the sheet may exhibit improved flexibility and/or may be less brittle than prior art sheets.

In certain embodiments, it may be necessary or desirable to incorporate into the sheet a scaffold to increase the mechanical strength and/or flexibility of the film for a particular application. Thus, in another aspect of the invention there is provided a tissue-adhesive sheet comprising a homogenous, preformed and cross-linked matrix applied to a scaffold material, said matrix being formed from one or more polymers, at least one of said one or more polymers being a synthetic polymer and having appendant functional groups of a first form, cross-linking of said matrix being via a proportion of said functional groups of the first form, and the remainder of said functional groups of the first form being free.

Suitable scaffolds are preferably composed of biocompatible and biodegradable material. The scaffold conveniently has the form of a sheet of material, the homogeneous, preformed and cross-linked matrix being applied to one or both sides of the sheet. In such a case, the product has a multilamellar form. The scaffold may be continuous or may be apertured. Most preferably, the scaffold is perforated. In particularly preferred embodiments, the scaffold sheet is formed with an array of perforations and the homogenous film is applied to one or both sides of the scaffold sheet.

Other embodiments of the invention have the form of three-dimensional articles that may be implanted in the body. Thus, in another aspect of the invention, there is provided a three-dimensional implantable article, said article comprising a preformed and cross-linked matrix formed from one or more polymers, at least one of said one or more polymers being a synthetic polymer and having appendant functional groups of a first form, cross-linking of said matrix being via a proportion of said functional groups of the first form, and the remainder of said functional groups of the first form being free.

Three-dimensional articles of this form may, for instance, have the form of plugs, pellets or pledgets.

The invention may also find application in the provision of an adhesive coating to an implantable medical device. In a further aspect of the invention, therefore, there is provided an implantable medical device, at least part of the external surface of which bears a coating comprising a cross-linked matrix formed from one or more polymers, at least one of said one or more polymers being a synthetic polymer and having appendant functional groups of a first form, cross-linking of said matrix being via a proportion of said functional groups of the first form, and the remainder of said functional groups of the first form being free.

In the following detailed description of the invention, reference is made primarily to embodiments of the invention that have the form of sheets. It will be appreciated, however, that analogous comments apply, where appropriate, to embodiments of the invention involving scaffolds, three-dimensional implantable articles or coatings on implantable devices.

In another aspect, the invention also provides a method of joining a tissue surface to another tissue, or of sealing a tissue surface, which method comprises applying to the tissue surface a sheet according to the first aspect of the invention.

The sheet according to the invention may be used for the delivery of one or more therapeutically active agents to the site to which the sheet is applied. In such a case, the active agent(s) may be incorporated into the sheet, eg by admixture with the other ingredients that are used in the manufacture of the sheet. Alternatively, the active agent(s) may be covalently bound to a component of the formulation. However, in other embodiments, the sheet is free of therapeutically active agents.

DETAILED DESCRIPTION OF THE INVENTION

Figure 1:
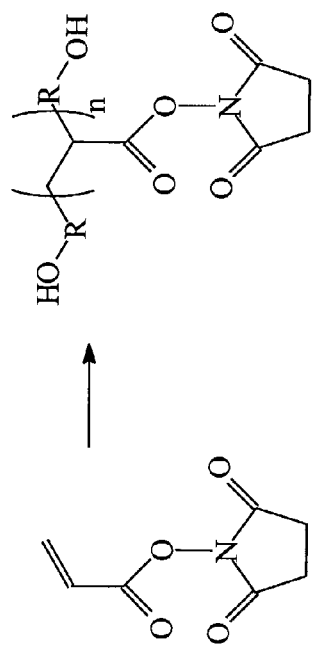
FIG. 1 represents the polymerisation of acrylic acid N-hydroxysuccinimide ester to yield a hydroxyl functional polymer.

| Abbreviations | |
|---|---|
| AAc | acrylic acid |
| AIBN | azo-iso-butyronitrile |
| CMC | carboxymethyl cellulose |
| DCC | dicyclohexylcarbodiimide |
| DCU | dicyclohexylurea |
| DEAE-dextran | diethylaminoethyl-dextran |
| DMF | dimethylformamide |
| ENT | ear, nose and throat |
| HEMA | hydroxyethyl methacrylate |
| HPC | hydroxypropylcellulose |
| HPC-terpolymer | a conjugate of HPC cross-linked with PEG dicarboxylic acid and coupled to poly(VP-AAc-AAc(NHS) moieties |
| HPMC | hydroxypropyl methylcellulose |
| $M_n$ | number average molecular weight |
| $M_w$ | weight average molecular weight |
| $DP_n$ | degree of polymerisation |
| NHS | N-hydroxysuccinimide |
| PCL | polycaprolactone |
| PEEK | polyetherketone |
| PEG | polyethylene glycol |
| PTFE | polytetrafluoroethylene |
| PHBV | polyhydroxybutyrate-valerate |
| PLG | poly(DL-lactide-co-glycolide) |
| poly(VP-AAc) | copolymer of vinyl pyrrolidone and acrylic acid |
| poly(VP-AAc(NHS) | copolymer of vinyl pyrrolidone and acrylic acid NHS ester |
| poly(VP-AAc-AAc(NHS)) | terpolymer of vinyl pyrrolidone, acrylic acid and acrylic acid NHS ester |
| PVOH | polyvinyl alcohol |

Nature of the One or More Polymers

The sheet comprises one or more polymers that are cross-linked (during manufacture) to form a matrix. At least one polymer is synthetic and comprises appendant functional groups of the first form.

The functional groups of the first form may fulfil three roles in the matrix:
a) a proportion of the functional groups of the first form are involved in cross-linking;
b) at least some of the remainder of the functional groups of the first form remain free and may provide for good contact adhesion between the sheet and the tissue to which it is applied (ie bioadhesive properties); and
c) to promote the formation of covalent bonds between the matrix and the surface of the tissue to which it is applied, some of the free functional groups of the first form may be in a derivatised or activated form so that they constitute tissue-reactive groups, and/or may be coupled to other moieties containing tissue-reactive groups.

Hydroxyl or carboxyl groups may fulfil all three of the roles referred to above, and so it is strongly preferred that the or each synthetic polymer having functional groups of a first form should have appendant hydroxyl or appendant carboxyl groups.

Preferred synthetic polymers having appendant hydroxyl groups, for use in the invention, are synthetic polysaccharides, preferably cellulose derivatives, and more preferably cellulose ethers. The most preferred synthetic polymer having appendant hydroxyl groups is hydroxypropylcellulose (HPC).

Preferred examples of synthetic polymers that have appendant carboxyl groups, for use in the invention, include poly (acrylic acid), poly(methacrylic acid) and poly(VP-AAc).

Poly(acrylic acid) is one particularly preferred synthetic polymer for use in accordance with the invention. Suitable grades of poly(acrylic acid) are available under the trade name Carbopol.

Poly(acrylic acid) with a molecular weight greater than 250,000 has been found to exhibit particularly good adhesive performance. Initial studies with formulations comprising poly(acrylic acid) of the grade sold as Carbopol 907 (which has a molecular weight, $M_w$, of approximately 500,000) produced a sheet with excellent adhesion, elasticity and flexibility by a simple method of manufacture. For many applications, however, particularly applications in which the sheet is used internally of the body, it may be preferable to employ material containing relatively low molecular weight poly (acrylic acid) or material that will degrade to yield poly (acrylic acid) with a relatively low molecular weight.

Such materials may, for example, take one of the following two general forms:
1) a high molecular weight poly(acrylic acid) polymer comprising relatively low molecular weight moieties connected by biodegradable linkages;
2) a high molecular weight polymer comprising relatively low molecular weight poly(acrylic acid) chains that are linked via biodegradable linkages to a polymer backbone.

Typically, the poly(acrylic acid) moieties or chains incorporated into such materials will have molecular weights $M_w$ of less than 10,000, more preferably less than 5,000, eg about 2,000.

In one method, a material of the first general form, consisting of low molecular weight (eg $M_w \leq 2,000$) poly(acrylic acid) connected via alkylene diester linkages, may be synthesised by protection of the acid moiety on the poly(acrylic acid), reaction with a diacyl chloride, and then removal of the protecting group.

Figure 2:
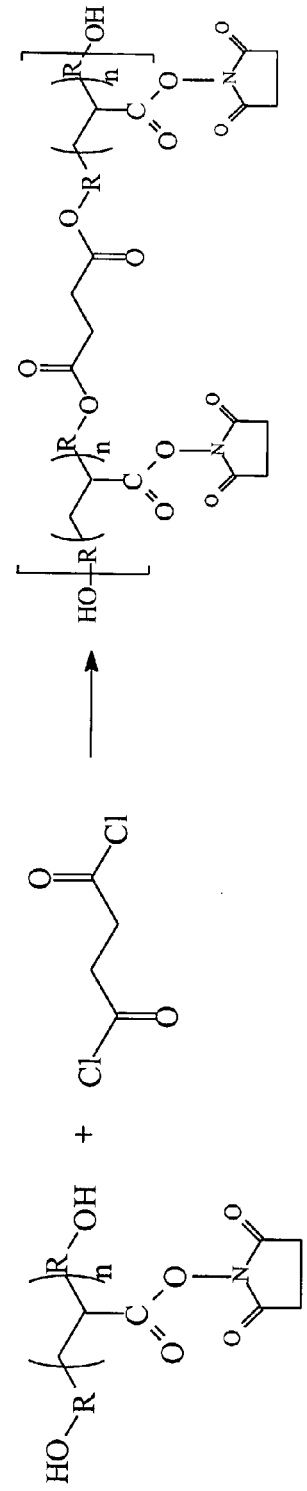
FIG. 2 shows coupling of the hydroxyl functional polymer of FIG. 1 by reaction with succinyl chloride.
Figure 3:
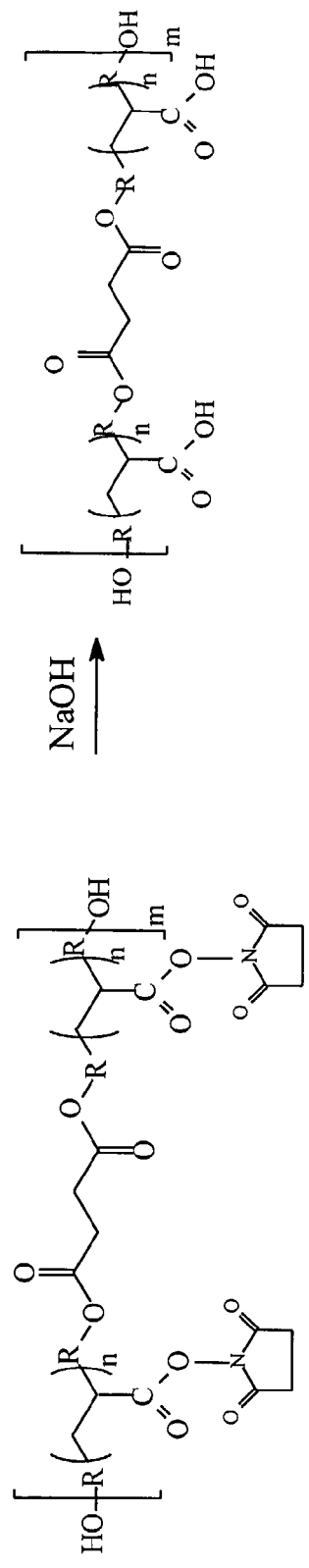
FIG. 3 illustrates the removal of NHS groups from the coupled polymer of FIG. 2 by base hydrolysis.

In another method, acrylic acid N-hydroxysuccinimide ester may be polymerised (eg using a hydroxyl functional initiator such as VA-086, supplied by Wako Chemicals) to yield an $\alpha,\omega$-dihydroxyl functional polymer (see FIG. 1, in which R—OH represents a residue derived from the initiator used, eg —C(CH$_3$)$_2$CONHCH$_2$CH$_2$OH in the case of VA-086, and n may have a wide range of values). This can then be reacted with succinyl chloride to yield a polymer with hydrolytically susceptible linkages along the backbone (FIG. 2, in which m is typically 100-150). Removal of the NHS groups by base hydrolysis yields a polymer consisting of poly(acrylic acid) units connected via biodegradable linkages (FIG. 3). Preferably, the molecular weight of the polymer is 250,000 or greater.

Materials of the second general form, in which poly(acrylic acid) chains are linked via a biodegradable linkage to a polymer backbone, may be synthesised via graft co-polymerisation.

Figure 4:
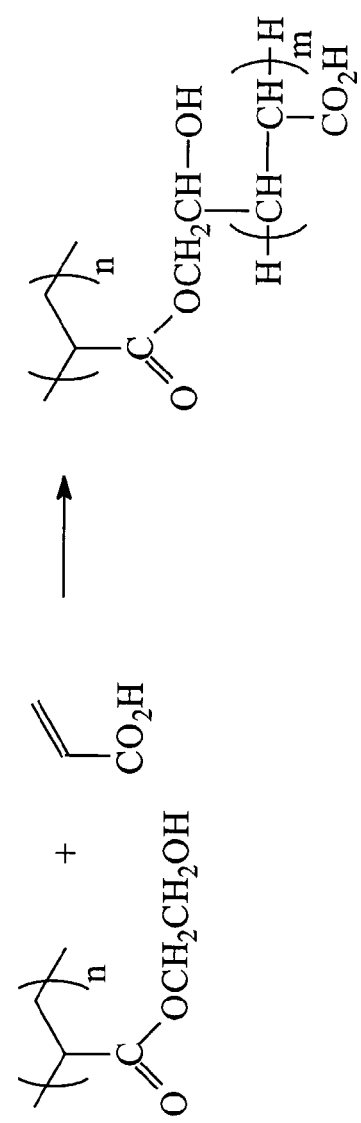
FIG. 4 shows the graft polymerisation of acrylic acid to a hydroxyl-functional polymer using cerium (IV).

In one suitable method of synthesis the proton on the carbon atom adjacent to a hydroxyl functionality may be abstracted using cerium (IV) to provide a site for free radical growth (FIG. 4, in which m have a wide range of values). The addition of acrylic acid with the correct stoichiometry will produce poly(acrylic acid) grafted to the hydroxyl functional material. This can take place on any polymer that is soluble in water, for example poly(acrylic acid) may be grafted on to a poly(HEMA) backbone. Other examples of hydroxyl functional materials that may be used include $\alpha,\omega$-dihydroxy PEG, polysaccharides such as HPC, CMC, HPMC, chitosan, PVOH etc. Furthermore, it may be possible to use similar reactions to graft poly(acrylic acid) chains onto carbon atoms that are adjacent to oxygen atoms in polyethers such as $\alpha,\omega$-dimethoxy PEG.

Figure 5:
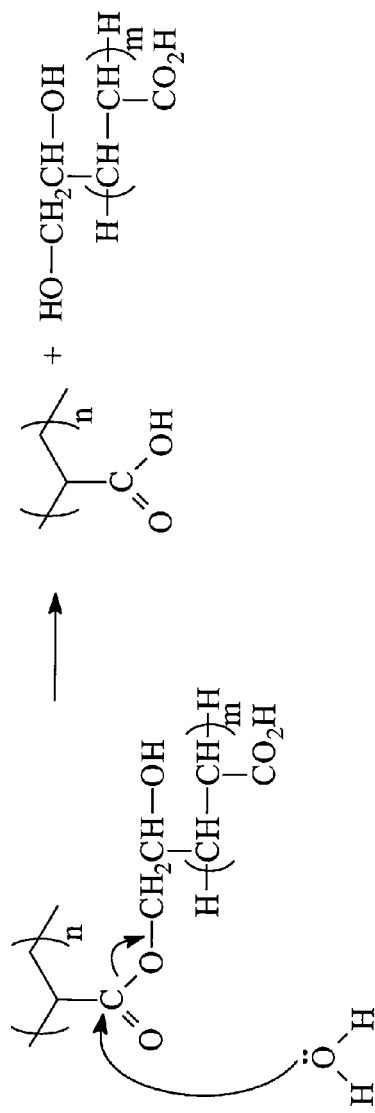
FIG. 5 shows a mechanism by which the graft copolymer of FIG. 4 may degrade in vivo.

In the product shown in FIG. 4, ester groups link the poly (acrylic acid) chains to the polymer backbone. These linking groups are susceptible to hydrolysis and therefore these functional materials may biodegrade as shown in FIG. 5.

Figure 6:
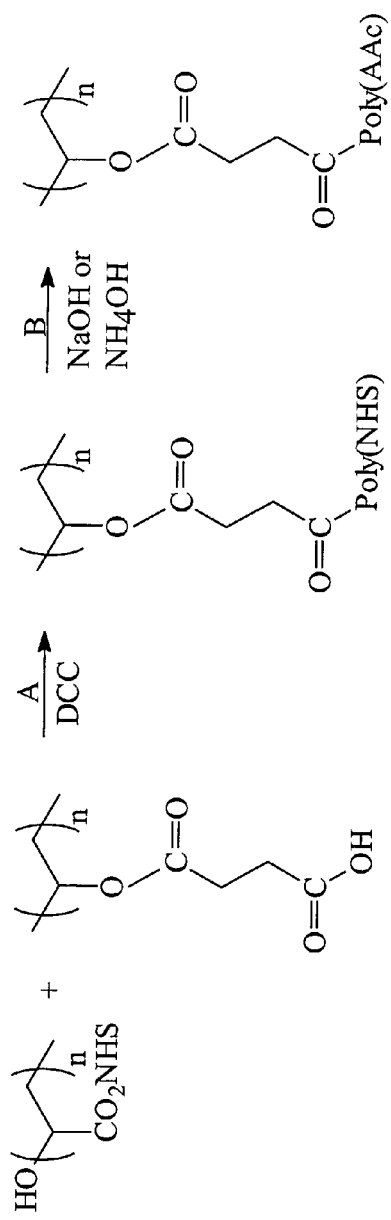
FIG. 6 outlines the synthesis of a biodegradable polymer based on poly(acrylic acid).

A further method of producing a biodegradable poly (acrylic acid)-containing material of the second general form is outlined in FIG. 6.

First, synthesis of a hydroxyl functional poly(acrylic acid-NHS) with a suitable molecular weight (DPn$\leq$30) may be carried out as shown in FIG. 1. The product of this reaction may then be coupled to a carboxylic acid functional polymer (eg HPC-succinate, PVOH-succinate, poly(acrylic acid) etc) using a carboxyl group activator, for example DCC (see FIG. 6, step A). The NHS is readily hydrolysed (FIG. 6, step B) to leave poly(acrylic acid) connected to an inert or non toxic polymer backbone via a hydrolysable linkage.

Materials of the second general form may also be synthesised by introducing acid functionality into a polymer comprising appendant hydroxyl groups, eg poly(vinyl alcohol). Acid functionality can be introduced into such polymers by the addition of a chain-extending group that terminates in a carboxyl group. This may be achieved by reaction of the poly(vinyl alcohol) with a cyclic anhydride (eg succinic anhydride) in the presence of a base such as pyridine or 4-dimethylaminopyridine.

The synthetic polymer (or synthetic polymers if there are more than one) used to form the cross-linked matrix may comprise further appendant groups, in addition to the functional groups of the first form. One example of such a synthetic polymer is poly(N-vinyl-2-pyrrolidone-co-acrylic acid) copolymer poly(VP-AAc), in which the molar ratio of acrylic acid-derived units is preferably between 0.20 and 0.80, and hence that of the vinyl pyrrolidone-derived units is between 0.80 and 0.20. Most preferably, the molar ratio of both acrylic acid-derived units and vinyl pyrrolidone-derived units in the copolymer fall within the range 0.35 to 0.65.

In such a case, the further appendant groups may contribute to the bioadhesive properties of the matrix. For example, where the matrix comprises derivatised PVP or a derivatised copolymer of vinyl pyrrolidone with another monomer (eg acrylic acid), the pendant pyrrolidone groups will contribute to the immediate contact adhesion (believed to be due to hydrogen and/or van der Waals bonding, as described above).

The synthetic polymer(s) from which the matrix is formed will generally have overall molecular weights $M_w$ in excess of 100,000, and more usually in excess of 200,000 and often in excess of 300,000.

Tissue-Reactive Groups

As described above, some of the free functional groups of the first form, which in preferred embodiments of the invention are hydroxyl or carboxyl groups, may (if they are not tissue-reactive groups) be converted to tissue-reactive functional groups.

By "tissue-reactive functional groups" is meant functional groups capable of reacting with other functional groups present in the tissue surface so as to form covalent bonds between the formulation and the tissue. Tissues generally consist partly of proteins, which commonly contain thiol and primary amine moieties. Many functional groups such as imido ester, p-nitrophenyl carbonate, NHS ester, epoxide, isocyanate, acrylate, vinyl sulfone, orthopyridyl-disulfide, maleimide, aldehyde, iodoacetamide, and others, may react with thiols or primary amines, and therefore constitute "tissue-reactive functional groups". As used herein, the term NHS or NHS ester is intended to encompass not only N-hydroxysuccinimide itself, but also derivatives thereof in which the succinimidyl ring is substituted. An example of such a derivative is N-hydroxysulfosuccinimidyl and salts thereof, particularly the sodium salt, which may increase the solubility of the tissue-reactive material.

Tissue-reactive functional groups that may be of utility in the present invention are any functional groups capable of reaction (under the conditions prevalent when the formulation is applied to tissue, ie in an aqueous environment and without the application of significant amounts of heat or other external energy) with functional groups present at the surface of the tissue. The latter class of functional group includes thiol and amine groups, and tissue-reactive functional groups therefore include groups reactive to thiol and/or amine groups. Examples are:

imido ester;
p-nitrophenyl carbonate;
NHS ester;
epoxide;
isocyanate;
acrylate;
vinyl sulfone;
orthopyridyl-disulfide;
maleimide;
aldehyde; and
iodoacetamide.

NHS ester is a particularly preferred tissue-reactive functional group.

Preferably, only some of the functional groups of the first form will be activated to form the tissue-reactive functional groups.

In other embodiments of the invention, at least some of the free functional groups of the first form are coupled to one or more additional materials that contain tissue-reactive functional groups. Such additional materials are preferably polymers comprising appendant tissue-functional groups ("tissue-reactive polymers"). NHS ester is a particularly preferred tissue-reactive functional group, and therefore preferred tissue-reactive polymers are NHS ester-rich polymers. Particularly preferred tissue-reactive polymers are poly(VP-AAc (NHS)) and poly(VP-AAc-AAc(NHS)) terpolymer.

The term "functionalised" as used herein when referring to such synthetic polymers in which some of the free functional groups of the first form are either activated to form tissue-reactive functional groups, or reacted with additional materials that contain tissue-reactive functional groups, eg tissue-reactive polymers.

The degree to which the tissue-reactive functional groups of the matrix bind to tissue may be controlled by varying the proportion of the functional groups of the first form that are derivatised to form the tissue-reactive groups and/or linked via reaction to a tissue-reactive polymer(s).

The currently most preferred functionalised synthetic polymer is HPC-terpolymer (a conjugate of HPC cross-linked with poly(VP-AAc-AAc(NHS)), the synthesis of one example of which is described in Example M.

The adhesive properties of the sheet may be increased by inclusion of one or more tissue-reactive materials, in particular tissue-reactive polymers, in the formulation, in addition to the functionalised polymer containing the functional groups of the first form. The tissue-reactive groups present in such additional tissue-reactive polymers may be the same as or different to the tissue-reactive groups present in any functionalised synthetic polymer in the formulation. Preferred additional tissue-reactive polymers include poly(VP-co-AAc (NHS)) and poly(VP-AAc-AAc(NHS)) terpolymer.

Sufficiency of the degree of initial adhesion of a sheet to the tissue, by the bioadhesive polymer(s), can be quantitatively determined in vitro, for example by performing an adhesion strength test. This test is performed by allowing the sheet to adhere to a suitable substrate (secured in a fixed position), while the sheet itself is physically attached at a separate point to the load of a tensile testing apparatus, positioned so that, prior to the test, the sheet is not under load. The load cell is moveable along an axis substantially perpendicular to that along which the substrate is positioned. The test involves movement of the load cell away from the substrate, at a constant predetermined rate, until the sheet detaches from the substrate. The output of the test is a quantitative measure of the energy of adhesion for that sheet—ie the cumulative amount of energy required to break the interaction between the sheet and the substrate to which it is adhered. A suitable cumulative energy of adhesion for the sheet according to the invention would be not less than 0.5 mJ.

In certain embodiments of the invention, in which the functional groups of the first form are carboxyl groups, a preferred functionalised polymer is poly(VP-AAc-AAc (NHS)) terpolymer. The carboxyl groups on poly(VP-AAc) may be converted to NHS esters by reaction with NHS in the presence of DCC (see Example K). If the acid content of the poly(VP-AAc) is determined (in moles), the percentage conversion may be controlled by adding the desired mole percent of NHS.

Where the functional groups of the first form are hydroxyl groups, a preferred functionalised polymer is HPC succinate-NHS. In this case, some of the hydroxyl groups are activated with NHS via succinic acid linkage (see Example L).

In particularly preferred embodiments, in which the synthetic polymer having functional groups of a first form is hydroxypropylcellulose, it is particularly preferred that the polymer is functionalised with poly(VP-AAc-AAc(NHS)) terpolymer (which in this case constitutes a tissue-reactive polymer). The most preferable HPC-terpolymer conjugates are formed using a PEG diacid to cross-link the HPC followed by reaction between the acid groups on the terpolymer and some of the hydroxyl groups on the HPC. Particularly suitable PEG diacids are $\alpha,\omega$-dicarboxylic acid functional PEGs, most preferably poly(ethylene glycol)bis(carboxymethyl) ether.

Sheets of the present invention may comprise more than one synthetic polymer having functional groups of the first form. Additional synthetic polymers having functional groups of the first form are not necessarily functionalised. Thus, in a preferred embodiment, the sheet comprises a first, functionalised synthetic polymer (having functional groups of the first form, some of which are derivatised to form tissue-reactive groups) and a second synthetic polymer having functional groups of the first form which is not functionalised.

Although the functional groups of the first form on the second non-functionalised synthetic polymer may be chosen to provide some initial adhesion to biological tissue, the principal role of a non-functionalised polymer will be in cross-linking of the matrix and therefore in providing structural integrity to the sheet.

The properties of the tissue-adhesive sheet maybe optimised by inclusion of other polymers and additives.

Plasticizers

It may be desirable to improve the flexibility and/or wet-strength of the tissue-adhesive sheets of the present invention by the addition of one or more plasticizers. In particular, low molecular weight species such as glycerol and low molecular weight poly(ethylene glycol) (preferably $M_w$=200-600) may be incorporated into the formulations to increase flexibility. Such materials may increase the flexibility of the sheet when added at levels of up to 30% by weight of the ingredients that make up the sheet. However, the inclusion of high levels of such materials may have a detrimental effect on the adhesive performance of the sheet.

To offset this disadvantage, preferable plasticizers are functional materials that include tissue-reactive groups, such as α,ω-di-NHS ester functional poly(ethylene glycol) and citric acid NHS ester, that may participate in tissue-adhesion.

Animated or Thiolated Polymers

Preferably, the sheet according to the invention is entirely synthetic, or substantially so, being free or substantially free of materials of human or animal, particularly mammalian, origin. By this is meant that the sheet contains less than 10% w/w, more preferably less than 5% w/w, less than 1% w/w or less than 0.1% w/w of such materials.

However, it has been found that the addition of small quantities of one or more animated and/or thiolated polymers may improve the structural integrity of tissue-adhesive sheets of the invention, especially when hydrated, as well as improving flexibility and adhesion to tissue. Some such polymers are of natural origin, or are derived from naturally occurring materials. Suitable animated polymers of natural origin include certain polysaccharides and proteins. Albumin is an example of a suitable protein. However, because of the risk or perceived risk associated with transmission of pathogens, non-proteinaceous animated polymers are preferred. Preferred examples of suitable polysaccharide materials include diethylaminoethyl-dextran (DEAE-dextran) and, more preferably, chitosan or chitosan oligosaccharide (which may also exhibit haemostatic properties). PEG derivatives may be suitable, eg PEG functionalised with amine and/or thiol groups, and polyvinylamines and polyallylamines may also be of benefit if they are biocompatible.

The preferred percentage of animated (or thiolated) polymer in the formulation will depend on the density of amine (or thiol) groups in the polymer. However, the animated or thiolated polymer is preferably present at a level of less than 10% by weight of the ingredients that make up the sheet.

It is desirable for the animated (or thiolated) polymer(s) not to react with tissue-reactive groups in the formulation during manufacture of the sheet because this would reduce the number of groups available for reaction with the tissue surface, lessening the bio-adhesion of the sheet. Thus, particularly preferred animated polymers are insoluble in the solvent that is used to dissolve the other components of the formulation in the manufacturing process (most conveniently, the matrix may be prepared by dissolving or dispersing the components of the matrix in a suitable solvent and casting the resulting solution into a suitable mould or onto a suitable plate).

For example, finely milled chitosan, chitosan oligosaccharide, diethyl amino ethyl dextran and albumin form fine suspensions in 15/4 v/v dichloromethane/methanol and such suspensions are not reactive in the short term with solutions containing NHS ester materials.

Buffers

Figure 7:
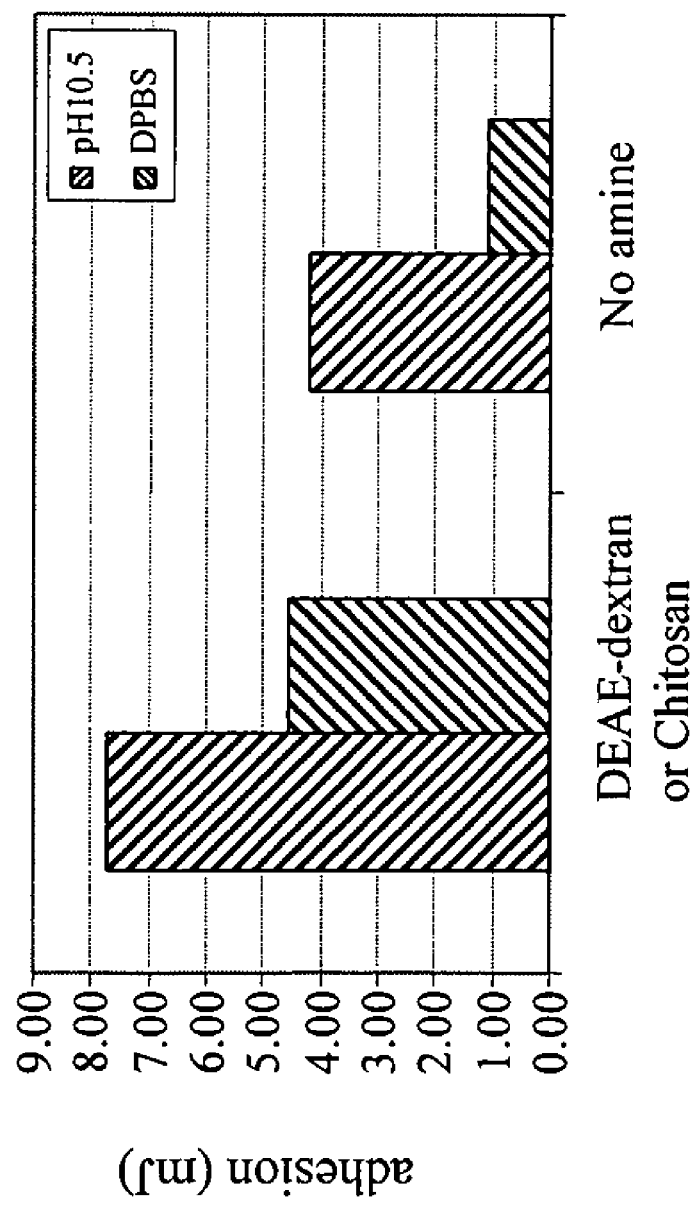
FIG. 7 is a plot showing mean work of adhesion to explanted porcine liver of tissue-adhesive sheets of the present invention.

The reaction between functional groups on the sheets of the present invention and functional groups on the surface of the tissue may vary with pH. It may therefore be preferable to buffer the tissue surface immediately prior to application or, more preferably, to include a buffer in the formulation. Experimental work has shown that mean work of adhesion of certain sheets according to the invention to explanted porcine liver is improved by buffering the tissue surface with pH 10.5 phosphate/carbonate buffer (FIG. 7 and Example P).

More preferably the buffer would be incorporated into the formulation, if required, probably by lyophilising the animated polymer from a buffer solution.

Other Additives

Non-adhesive additives may be included to improve the flexibility and strength of the sheet. It is anticipated that any film-forming polymer that is biocompatible and biodegradable may be suitable. Preferred additives include PHBV which is sold commercially under the trade name Biopol®, and PCL. However, the most preferred additive of this nature is PLG.

Such additives are preferably included at levels of between 0 and 10% by weight of the ingredients that make up the bioadhesive sheets of the present invention. More preferably the level of such additives is about 3% by weight of the ingredients.

Cross-Linking of the Matrix During Manufacture

The matrix is cross-linked primarily by coupling together molecules of the synthetic polymer(s) via a proportion of the functional groups of the first form. Such cross-linking increases the physical strength of the matrix and may be tailored to optimise the properties of the sheet, in particular in terms of the time required for biodegradation of the sheet after it has been applied.

Cross-linking of the matrix may be brought about by various means. Most preferably, however, at least one component is included in the formulation from which the sheet is prepared that comprises at least two functional groups which are capable of reacting with the first form of functional group present on the synthetic polymer(s) from which the matrix is formed. This component will therefore be acting as a cross-linking agent. Preferably, the cross-linking agent contains at least two functional groups of the same form. Thus, the cross-linking agent is most preferably a homobifunctional or homopolyfunctional cross-linking agent.

As mentioned above, a preferred type of functional group of the first form is a hydroxyl group or a carboxyl group. The condensation reaction between hydroxyl and carboxyl groups to form ester linkages is particularly suitable for crosslinking components to form the matrix according to the invention.

In certain preferred embodiments of the invention where the functional groups of a first form are carboxyl group, cross-linking is preferably effected by reaction of the carboxyl groups with hydroxyl groups on one or more components in the formulation. Polyalcohols are particularly preferred cross-linking agents in this case. Examples of such polyalcohol cross-linking agents include sucrose, glycerol and PEGs, mentioned above for their use as plasticizers.

It may be particularly beneficial for combinations of cross-linking agents to be employed in the manufacture of the sheet, in order to optimise the properties of the sheet. Thus, the properties of the sheet may be varied by the use of different cross-linking agents (eg PEGs of different molecular weights), different proportions of bifunctional cross-linking agents (eg PEG and glycerol) and polyfunctional cross-linking agents (eg sucrose).

In other preferred embodiments where the functional groups of a first form are hydroxyl groups, cross-linking is preferably effected by reaction of the hydroxyl groups with carboxyl groups on one or more components in the formulation. One particularly preferred component of formulations in which hydroxyl groups are the functional groups of the first form is poly(VP-AAc-AAc(NHS)) terpolymer. A functionalised synthetic polymer in the formulation may comprise poly(VP-AAc-AAc(NHS)) terpolymer groups and/or the poly(VP-AAc-AAc(NHS)) terpolymer may be present in the formulation as an additional tissue-reactive polymer.

Physical Form of the Sheet

The sheet may typically have an overall thickness of from 0.01 to 1 mm, typically 0.01 to 0.5 mm, and more commonly 0.02 to 0.4 mm, eg about 50 μm or 100 μm or 200 μm.

The sheet may be produced with, or subsequently cut to, dimensions of from a few square millimeters up to several tens of square centimeters.

Optionally, a surface of the sheet that, in use, is not intended to adhere to tissue may be coated with a non-adhesive material. Most preferably, such a material is a synthetic polymer. Examples of suitable polymers include PEGs, polylactide and PLG. A sheet with such a non-adhesive coating will adhere only to the target tissue (to which the underside of the sheet is applied) and not to surrounding tissues (eg the pleural or peritoneal wall). Such a non-adhesive coating will typically have a thickness of 10-50 μm. The non-adhesive coating may include a visibly-absorbing chromophore to enable identification of the non-tissue contacting surface of the sheet. An example of a suitable chromophore is methylthioninium chloride.

As noted above, in certain embodiments the inclusion of a scaffold material may be desired to improve the mechanical strength and/or flexibility of the sheet for a particular application, or to re-enforce a particular portion of the sheet. The scaffold may be present as a backing or coating on the sheet, or as a central core encapsulated by the matrix. Suitable scaffolds may be perforated or unperforated, preferably perforated. Preferable scaffold materials include polyvinyl alcohols, polyesters, PTFE, PEEK, and polylactides (provided that they do not dissolve in the solvent that is used to dissolve the synthetic polymer(s) and other components in the manufacture of the cross-linked matrix).

Manufacture of the Sheet

Most conveniently, the matrix may be prepared by dissolving or dispersing the components of the matrix in a suitable solvent, and casting the resulting solution into a suitable mould or onto a suitable plate. Most preferably, this is followed by drying to remove solvent, and curing to achieve the desired degree of cross-linking. Curing is most preferably promoted by prolonged application of elevated temperatures (typically several hours at temperatures in excess of 60° C.).

Once manufactured, and prior to use, the sheet according to the invention will typically have a water content of less than 10% w/w, and more commonly less than 5% w/w.

Three-dimensional articles may similarly be prepared by filling of moulds with liquid formulations.

Sheets comprising a structural scaffold may be prepared by casting the liquid formulation onto the scaffold, by dipping of the scaffold in the liquid formulation or by spraying the formulations onto the scaffold. If the scaffold is required as a backing on one side of the sheet, it may be added during or after the curing process.

Likewise, coatings may be applied to medical devices by casting the formulation over the device, dipping of the devices in liquid formulations or by spraying the devices with the liquid formulation.

Sheets and other formulations according to the invention may typically be made up from the following ingredients in the proportions indicated:

Synthetic polymer(s) with functional groups of the first form: preferably 20-80% w/w, more preferably 20-70% w/w, 30-60% w/w or 40-60% w/w;

Additional synthetic polymer(s): preferably 0-30% w/w, more preferably 0-20% w/w or 5-20% w/w;

Plasticizer(s): preferably 0-30% w/w, more preferably 10-30% w/w or 10-20% w/w;

Animated and/or thiolated polymer(s): preferably 0-10% w/w, more preferably 2-8% w/w;

Non-adhesive film-forming polymer(s): preferably 0-10% w/w, more preferably 0-5% w/w.

Therapeutic Applications of the Sheet

The sheet according to the invention is suitable for application to both internal and external surfaces of the body, ie it may be applied topically to the exterior of the body (eg to the skin) or to internal surfaces such as surfaces of internal organs exposed during surgical procedures, including conventional and minimally invasive surgery.

The sheet according to the invention is particularly suitable for surgical applications in the following areas:

Thoracic/cardiovascular
General surgery
ENT
Urology
Oral/maxillofacial
Orthopaedic
Neurological
Gastroenterology
Opthalmology
Gynaecology/obstetrics Possible uses are described in more detail below.

Wound Healing

The degradable nature of the sheet means that it may support and promote wound healing during both internal and topical procedures. Once the sheet begins to degrade, fibroblasts will move in and begin to deposit components of the extracellular matrix. The sheet can therefore be used as an internal or external dressing. In addition, factors such as growth factors and cAMP that are known to promote the proliferation of skin cells may be added to the formulation to assist in the healing process. The sheet may be designed to control the transmission of moisture and infectious agents, and thus be useful particularly in the treatment of burns.

Skin Closure

The sheet may be applied topically to promote wound closure (as an alternative to sutures). This may have beneficial effects in that it may reduce scarring, and the formulation and sheet may thus be useful for cosmetic purposes during minor surgery (eg in Accident and Emergency Departments). The self-adhesive properties of the sheet make it easy to apply quickly.

Hernia Repair

The sheet may be used to provide reinforcement in hernia repair procedures. The self-adhesive attachment overcomes the potential issues faced by conventional surgical reinforcing mesh products, which require suturing or stapling in an already weakened area. The sheet for such a procedure may be engineered to have short or long term durability, depending on the degree of tissue repair required. The sheet may also be able to withstand the application of staples.

The invention may also find application in the provision of an adhesive coating to hernia mesh devices.

Anastomosis

The self-adhesive sheet provides a means for rapid sealing of, and prevention of leaks in, joined tubular structures such as blood vessels, and vascular and bladder grafts, and the GI tract. The ability of the sheet to support tissue repair may be of particular value if used in nerve repair.

Sealing Large Areas of Tissue

The good sealing and handling properties of the sheet, combined with its self-adhesive properties and ability to cover a large surface area, mean that it may be of particular use in sealing resected tissue surfaces—in particular those where diffuse bleeding is an issue (eg the liver). The sheet also provides an ideal support matrix for tissue repair at such sites. This could also be applicable to limiting leakage of cerebrospinal fluid following neurological surgery.

Sealing Air Leaks

In addition to the patch properties described above, the high tensile strength and good inherent elasticity of the sheet (after hydration and reaction of the tissue-reactive functional groups), make it particularly suitable for sealing air leaks in the lung, particularly following lung resection. Again, after effecting a seal, the sheet provides an ideal support matrix for tissue repair at such sites.

Haemostasis

The sheet may be applied to a bleeding area, acting as a physical barrier. The tissue-reactive material in the sheet may immobilize proteins and thereby promote haemostasis.

Therapeutic Agent Administration

Drugs and other therapeutic agents (including biologically active agents such as growth factors, and even cells and cellular components) may be added to solution(s) used to form the components of the sheet, or covalently linked to components prior to their use in the manufacture of the sheet. Once the sheet is in place, following application to the desired site, the drug will be slowly released, either by diffusion or by engineering the sheet so that as it degrades over time the drug is released. The rate of release can be controlled by appropriate design of the sheet. The sheet may thus provide a means for delivering a known amount of drug either systemically or to a precise locus. The drug may be directly bound to a component of the formulation, or simply dispersed in the formulation.

Prevention of Post-Surgical Adhesions

Post-surgical adhesion, the formation of undesired connective tissue between adjacent tissues, is a serious problem which can give rise to major post-surgical complications. It is a particular problem in bowel surgery where it can cause, for instance, twisting of the bowel, which may then necessitate further surgical intervention. The application of sheet material having self-adhesive properties in accordance with the invention to tissues exposed in a surgical procedure can be effective in preventing post-surgical adhesions between that tissue and neighbouring tissues.

Minimally Invasive Procedures

The use of minimally invasive techniques for taking tissue samples by biopsy, inserting devices, delivery of therapeutic agents and performing surgical procedures is rapidly developing as an alternative choice to traditional "open" surgery. Minimally invasive procedures typically result in less pain, scarring, quicker recovery time and fewer post-operative complications for patients, as well as a reduction in health care costs. Procedures are undertaken using specially designed instruments which are inserted through small keyhole-sized surgical incisions. The sheet may be introduced into the body via existing and specially designed minimally invasive surgery instruments and trocar systems, and the sheet may be shaped or prepared to an appropriate size and configuration. The format of the formulation also may be modified to enable delivery of powders, tablets, pellets, tapes/strips/plegets and other 3-D matrices. The use of a self adhesive formulation will significantly reduce the technical difficulties associated with manipulating, closing and repairing tissues where access is restricted. In addition the sheet properties make them particularly suitable for sealing leaks of air, blood or fluid or for delivery of therapeutic agents. The thin and flexible form of the sheet and other three-dimensional matrices according to the invention may render them particularly useful for minimally invasive surgery procedures.

DETAILED DESCRIPTION OF PREFERRED EMBODIMENTS

The invention will now be described in greater detail, by way of illustration only, with reference to the following Examples.

Example A

General Method for the Preparation of Bioadhesive Sheets Using Functionalised HPC

| | |
|---|---|
| Functionalised HPC | 1.0 g |
| Non-adhesive additive | 0.1 g |
| Tissue-reactive polymer | 0.6 g |
| Non-functionalised synthetic polymer | 0.5 g |
| Plasticizer | 1.0 g |
| Aminated polymer | 0.2 g |

Sheets made using this formulation are produced by dissolving the components, with the exception of the animated polymer in 15/4 v/v dichloromethane/methanol (DCM/MeOH). Once fully mixed, they are combined with a suspension of the animated polymer in the same solvent. The sheets are dried at approximately 40° C. until dry and then at 90° C. under vacuum for 3-4 hours to provide further cross linking via the condensation of acid functionalities with alcohol functionalities present in the constituent polymers.

Particular materials that may be used include the following:

| | | |
|---|---|---|
| Functionalised HPC | HPC-terpolymer conjugate of Example M | 1.0 g |
| Non-adhesive additive | poly(DL-lactide-co-glycolide) as supplied by Purac Biochem BV (Gorinchem, The Netherlands) as 50/50PDLG. Approximate molecular weights, $M_n = 70,000$, $M_w = 200,000$ | 0.1 g |
| Tissue-reactive polymer | poly(VP-AAc-AAc(NHS)) terpolymer of Example K | 0.6 g |
| Non-functionalised synthetic polymer | HPC purchased from Sigma Aldrich (catalogue number 19,189-2), $M_w = 370,000$ | 0.5 g |
| Plasticizer | PEG-200 purchased from Sigma Aldrich (catalogue number 20,236-3) | 1.0 g |
| Aminated polymer | Chitosan oligosaccharide lactate purchased from Sigma Aldrich (catalogue number 52,368-2), $M_n = <5,000$ | 0.2 g |

Examples B-D

Preferred Formulations Used to Produce Bioadhesive Sheets Using Poly(Acrylic Acid)

Sheets in accordance with the invention were prepared by dispersing the following ingredients, at the concentrations shown, in 100 ml of 50:50 acetone:water:

|  | % w/w | | |
| --- | --- | --- | --- |
|  | Example B | Example C | Example D |
| Carbopol 907 | 3 | 5 | 3 |
| Poly(VP-AAc-AAc(NHS))* | 2 | 0 | 2 |
| PEG 200** | 3 | 0 | 3 |
| sucrose | 2 | 2 | 4 |
| glycerol | 2 | 0 | 2 |

*a 50:50 copolymer of acrylic acid and N-vinyl pyrrolidone in which approximately one-half of the acrylic acid carboxyl groups are activated to form reactive NHS ester groups (as shown in Example K)

**polyethylene glycol of approximate relative molecular weight 200

The solution was poured into a PTFE-lined Petri dish or cast onto a PTFE plate and the acetone removed by heating at 40° C. for 16 hours. The sheet was subsequently cured for four hours at 90° C. (Examples B and C) or 8 hours at 90° C. (Example D).

The adhesion of the sheets to porcine liver was measured by placing a 15 mm×15 mm sample onto excised porcine liver. After 5 minutes, the sample was immersed in Dulbecco's phosphate-buffered saline for a further 5 minutes before being removed using a Zwick universal testing machine. This was also repeated with 30 minutes immersion and 90 minutes immersion.

The mean energy of adhesion for each formulation was as follows:

|  | Mean Energy of Adhesion/mJ (SD) | | |
| --- | --- | --- | --- |
| Example | 5 minutes immersion | 30 minutes immersion | 90 minutes immersion |
| B | 4.93 | 2.86 | 5.45 |
| C | 4.89 | 1.55 | 1.36 |
| D | 1.81 | 1.18 | 0.41 |

Without wishing to be bound by any particular theory, it is believed that the reduced adhesion of Example D may be attributable to higher than optimal cross-linking of the polymers due to the presence of relatively large amounts of the polyfunctional cross-linking agent (sucrose), and to higher than optimal concentration of non-adhesive plasticisers (sucrose and PEG). As a result, a high proportion of the carboxyl groups may be involved in the cross-linking, with a correspondingly reduced number of carboxyl and a reduced percentage of NHS ester groups being available to provide initial contact adhesion and longer term adhesion by reaction with the tissue respectively.

Examples E-I

Poly(Acrylic Acid)-Containing Materials that May be Incorporated into the Formulations Shown in Examples B-D Above, as a Direct Replacement for the Non-Functionalised Synthetic Polymer, Carbopol 907

In each case, poly(acrylic acid) is grafted onto a main polymer backbone, via a degradable linkage and with a combined molecular weight of poly(acrylic acid) of 250,000 or greater.

The methods of synthesis of Examples E-F are modified from covalent coupling of immunoglobulin G to a poly(vinyl alcohol)-poly(acrylic acid) graft polymer as a method of fabricating the interfacial-recognition layer of a surface plasmon resonance immunosensor (Disley D. M. et al, Biosensors and Bioelectronics (1998), Vol 13, No. 3-4 pp 383-396).

FIG. 4 shows the reaction between PVOH and acrylic acid in the presence of an oxidising agent, cerium (IV).

Example E

Graft Polymerisation of Acrylic Acid on High Molecular Weight PVOH 1 g of 145,000 molecular weight PVOH, 99-99.8% hydrolysed is dissolved in 500 ml of distilled water. The water is deoxygenated by bubbling oxygen free nitrogen through for at least 30 minutes. 24.5 g (0.34 moles) of acrylic acid is added to the polymer solution and nitrogen is bubbled through the solution for a further five minutes. 13.3 g (0.023 moles) of ammonium cerium (IV) nitrate is dissolved in 30 ml of 1.0M nitric acid and added to the polymer/acrylic acid solution with rapid stirring. The reaction is left under a nitrogen blanket for 18 hours at room temperature. The solution is filtered to remove catalyst residues and lyophilised to isolate the polymer.

Example F

Graft Polymerisation of Acrylic Acid on Low Molecular Weight PVOH 1 g of 9-10,000 molecular weight PVOH, 80% hydrolysed is dissolved in 500 ml of distilled water. The water was deoxygenated by bubbling oxygen free nitrogen through for at least 30 minutes. 36.32 g (0.50 moles) of acrylic acid is added to the polymer solution and nitrogen is bubbled through the solution for a further five minutes. 9.86 g (0.018 moles) of ammonium cerium (IV) nitrate are dissolved in 30 ml of 1.0M nitric acid and added to the polymer/acrylic acid solution with rapid stirring. The reaction is left under a nitrogen blanket for 18 hours at room temperature. The solution is filtered to remove catalyst residues and lyophilised to isolate the polymer.

Example G

Graft Polymerisation of Acrylic Acid on Chitosan (Reference: Studies on the degradation behaviour of chitosan-g-poly(acrylic acid) copolymers. Ming-Don et al, Tamkang Journal of Science and Engineering, Vol 5, No. 4, pp 235-240 (2002).)

1 g of chitosan is dissolved in 100 ml of deoxygenated distilled water and 13.7 ml (0.19 moles) of acrylic acid. The solution was heated to 70° C. in a water bath and 3.73 g (0.007 moles) of ammonium cerium (IV) nitrate dissolved in 5 ml of 1.0M nitric acid is added to the polymer/acrylic acid solution with rapid stirring. The solution is left overnight at 70° C. and excess catalyst removed by dialysis. The copolymer is isolated by lyophilisation.

Example H

Graft Polymerisation of Acrylic Acid on PEG

In this approach the cerium (IV) may abstract a proton from the carbon atoms adjacent to the PEG ether oxygen. This has been done using α,ω-dihydroxyl functional PEG, and also using dimethoxy terminal PEG.

PEG with a molecular weight of 10,000 was dissolved in 500 ml of distilled water. The water was deoxygenated by bubbling oxygen free nitrogen through for at least 30 minutes. 46.4 g (0.64 moles) of acrylic acid is added to the polymer solution and nitrogen is bubbled through the solution for a further five minutes. 13.4 g (0.024 moles) of ammonium cerium (IV) nitrate are dissolved in 30 ml of 1.0M nitric acid and added to the polymer/acrylic acid solution with rapid stirring. The reaction is left under a nitrogen blanket for 18 hours at room temperature. The solution is filtered to remove catalyst residues and lyophilised to isolate the polymer.

Example I

Graft Polymerisation of Acrylic Acid on Poly(HEMA 1 g of poly(2-hydroxyethyl methacrylate) ($M_w$ approx 20,000) is dissolved in 500 ml of deoxygenated water containing 15.4 g (0.008 moles) of acrylic acid. Oxygen free nitrogen is bubbled through the solution until all solids are completely dissolved. Once all solids are completely dissolved, 0.008 moles (4.2 g) of ammonium cerium (IV) nitrate dissolved in 8 ml of 1.0M nitric acid. The solution is stirred at 25° C. for 18 hours, filtered and lyophilised to isolate the p(HEMA)-g-P(AAc).

Example J

Preparation of Poly(VP-AAc(NHS))

600 ml of toluene is heated to 80° C. in a water bath whilst bubbling oxygen free nitrogen through the solvent for 30 minutes to remove dissolved oxygen. 64.88 g (0.58 moles) of N-vinyl pyrrolidone and 10.1 µg (0.14 moles) of acrylic acid are added to the toluene followed immediately by the addition of 0.144 g ($8.8 \times 10^{-4}$ moles) of AIBN dissolved in 3 ml of toluene. The reaction temperature is maintained at 80° C. for 17-19 hours under a nitrogen blanket. The polymer is isolated by precipitation from 3000 ml of 1:1 v/v hexane/diethyl ether followed by filtration under reduced pressure. The polymer is washed three times with 600 ml of diethyl ether before being dried under vacuum at 40° C. for 72 hours.

The acrylic acid content of the polymer is determined by titration against 1.0M NaOH. 50 g of poly(VP-AAc) containing 0.10 moles of acrylic acid is dissolved in 400 ml of N,N'-dimethylformamide. 0.10 moles (11.58 g) of N-hydroxysuccinimide is added to the solution and once all the solids have completely dissolved, 0.10 moles (20.74 g) of DCC dissolved in 25 ml of DMF is added to the reaction. The solution is stirred at 25° C. for at least 96 hours before being filtered to remove a reaction by product, dicyclohexylurea.

The polymer is isolated by precipitation from 3200 ml of 5:1 v/v hexane/iso-propanol and filtration under reduced pressure. The polymer is purified further by three successive washes with 425 ml of diethyl ether and then dried under reduced vacuum at 40° C. for 72 hours.

Residual amounts of contaminants such as solvents, unreacted monomer, DCC and DCU are removed by Soxhlet extraction using iso-propanol as the extraction solvent.

Example K

Synthesis of Poly(VP-AAc-AAc(NHS))Terpolymer 400 ml of toluene in a 500 ml round bottomed flask is heated using a thermostatted water bath set to 80° C. The toluene is deoxygenated by bubbling oxygen free nitrogen through the solvent for 30 minutes. 31.6 g (0.28 moles) of N-vinyl pyrrolidone and 20.6 g (0.28 moles) of acrylic acid are added to the toluene immediately followed by 0.1 g ($6.1 \times \times 10^{-4}$ moles) of 2,2'-azobis(2-methylpropionitrile). The reaction is left at 80° C. for 17-19 hours. The polymer is isolated by precipitation in 2000 ml of 1/1 v/v hexane/diethyl ether followed by filtration under reduced pressure. The polymer is washed three times with 300 ml of diethyl ether and finally dried under vacuum at 40° C.

The acid content of the poly(VP-AAc) copolymer is determined by titration against 1.0M sodium hydroxide. 50 mol % of the acid groups are converted to NHS ester by reaction with NHS in the presence of DCC. Briefly, 133.7 g of poly(VP-AAc) containing 0.77 moles of acrylic acid functionalities and 44.54 g (0.38 moles) of NHS are dissolved in 1000 ml of N,N'-dimethylformamide (DMF) at 25° C. 79.77 g (0.38 moles) of DCC is dissolved in 137 ml of DMF and added to the polymer solution and the reaction is stirred at 25° C. for 96 hours. The reaction by product, dicyclohexylurea is removed by filtration under reduced pressure using a 10-16 µm sintered glass funnel. The polymer is isolated by adding to 1250 ml of iso-propanol followed by precipitation from 5000 ml of diethyl ether followed by filtration. The polymer is washed three times in 1000 ml of diethyl ether and then dried at 40° C. under reduced pressure.

The polymer may be purified further to remove trace amounts of contaminants by a number of commonly know methods, for example, Soxhlet extraction, dialysis or washing with using a suitable solvent such as iso-propanol. Furthermore, drying at elevated temperature under reduced pressure may remove trace amounts of solvents and other volatile matter.

Approximate molecular weights $M_n$=2-5,000, $M_w$=10-30,000.

Example L

Synthesis of HPC Succinate-NHS 10 g of hydroxypropyl cellulose ($M_w$ approx 370,000) is dissolved in 350 ml of anhydrous N-methylpyrrolidone at 80° C. in a thermostatted water bath. 1.4 g (0.014 moles) of succinic anhydride is dissolved in the solution along with 1.71 g (0.014 moles) of 4-dimethylaminopyridine. The reaction is left overnight at 80° C. The solution is cooled to room temperature and 400 ml of iso-propanol is added. The polymer is precipitated from 3000 ml of diethyl ether, filtered and washed successively with 300 ml of diethyl ether. Finally, the polymer is dried under vacuum at 40° C.

This polymer is then dissolved in DMF and reacted with NHS in the presence of DCC to form the amine- and thiol-reactive NHS ester compound.

Example M

Preparation of HPC-Terpolymer Conjugate 5 g of hydroxypropyl cellulose and 18 g of the terpolymer described in Example K are dissolved in 200 ml of DMF. 2.3 g of poly(ethylene glycol)bis(carboxymethyl)ether (structure provided below) is added, followed by 1.3 g of DCC dissolved in 50 ml of DMF. The reaction is stirred for ten days at 25° C., following which the DCU by product is removed by filtration. The polymer solution is diluted with 500 ml of iso-propanol, precipitated from 500 ml of rapidly stirring diethyl ether and then isolated by filtration under reduced pressure. The polymer is washed three times using 500 ml of diethyl ether and then dried under reduced pressure at 40° C.

Structure of poly(ethylene glycol)bis(carboxymethyl) ether:

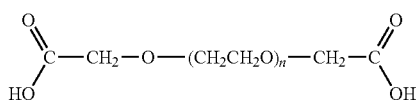

Examples N and O

Reactive Plasticizers

Example N

α,ω-di-NHS Ester Functional PEG 20 g of poly(ethylene glycol)bis(carboxymethyl)ether containing 0.067 moles of carboxylic acid moieties is dissolved in 200 ml of DMF. 7.7 g (0.067 moles) of N-hydroxysuccinimide is added to the vessel followed by 13.7 g (0.067 moles) of dicyclohexylcarbodiimide. The reaction is stirred at 25° C. for 24 hours and the dicyclohexylurea by-product is removed by filtration under reduced pressure. The DMF is removed by rotary evaporation and the product purified further by washing with diethyl ether successively to yield a straw coloured, viscous liquid. This is dried under vacuum at 40° C. to remove traces of diethyl ether.

Example O

Citric Acid NHS Ester (The method of synthesis is modified from that described in: Bonding of soft tissues using a novel tissue adhesive consisting of a citric acid derivative and collagen. Taguchi et al, Materials Science and Engineering C, Vol. 24, pp 775-780, 2004.)

10 g of citric acid containing 0.143 moles of carboxylic acid groups and 1634 g (0.143 moles) of NHS is dissolved in 350 ml of DMF. Once completely dissolved, 29.4 g (0.143 moles) of DCC is added to the reaction. DCU precipitate rapidly appears followed by a colour change from clear through yellow through orange to a deep red/brown. After 24 hours, the DCU was removed by filtration under reduced pressure using a 16-40 μm sintered glass funnel. The volume of DMF was reduced by rotary evaporation to leave a deep red coloured liquid.

Example P

Summary of Mean Work of Adhesion to Explanted Porcine Liver of Tissue-Adhesive Sheets of the Present Invention Formulated with and without Animated Polymers

|  | with amine | without amine |
| --- | --- | --- |
| pH 10.5 | 7.73 | 4.20 |
| DPBS | 4.57 | 1.07 |

Experimental work has shown that the mean work of adhesion of sheets according to the invention to explanted porcine liver is improved by buffering the tissue surface with pH 10.5 phosphate/carbonate buffer. This has been achieved by moistening the tissue surface with buffer prior to commencing adhesion testing. FIG. 7 and Table 2 show the effect on adhesion of buffering the tissue surface with pH 10.5 phosphate/carbonate buffer on formulations with and without animated polymers.

The invention claimed is:

1. A terpolymer of vinyl pyrrolidone, acrylic acid and acrylic acid N-hydroxysuccinimide ester.

2. A terpolymer as claimed in claim 1, wherein approximately one-half of the acrylic acid carboxyl groups are activated.

3. A terpolymer as claimed in claim 1, wherein the ratio of vinyl pyrrolidone to acrylic acid and acrylic acid N-hydroxysuccinimide ester together is 50:50.

4. A terpolymer according to claim 1, with a number average molecular weight of 2,000 to 5,000.

5. A terpolymer according to claim 1, with a weight average molecular weight of 10,000 to 30,000.

6. Hydroxypropylcellulose conjugated with a terpolymer as claimed in claim 1.

7. A method of preparing a terpolymer of vinyl pyrrolidone, acrylic acid and acrylic acid N-hydroxysuccinimide ester, which method comprises the following steps:
(a) preparing a copolymer of vinyl pyrrolidone and acrylic acid; and
(b) activating a proportion of the acrylic acid carboxyl groups using N-hydroxysuccinimide to form the acrylic acid N-hydroxysuccinimide ester, thereby forming the terpolymer according to claim 1.

8. A method as claimed in claim 7, wherein the ratio of vinyl pyrrolidone to acrylic acid in the copolymer is 50:50.

9. A method as claims in claim 7, wherein approximately one-half of the acrylic acid carboxyl groups are activated in step (b).

10. A tissue-adhesive sheet comprising:
a homogeneous film having at least one surface that, in use, is exposed, said film comprising a preformed and cross-linked matrix formed from one or more polymers comprising a terpolymer according to claim 1.

11. The tissue-adhesive sheet according to claim 10, wherein the terpolymer comprises tissue-reactive functional groups.

12. The tissue-adhesive sheet according to claim 10, wherein the one or more polymers further comprise hydroxypropylcellulose.

13. The tissue-adhesive sheet according to claim 12, wherein the hydroxypropylcellulose is conjugated with the terpolymer.

14. The tissue-adhesive sheet according to claim 10, wherein the sheet contains less than 10% w/w of materials of human or animal origin.

15. The tissue-adhesive sheet according to claim 10, wherein the sheet has an overall thickness of 0.01 to 1 mm.

16. The tissue-adhesive sheet according to claim 10, wherein the sheet has a water-content of less than 10% w/w.

17. The tissue-adhesive sheet according to claim 10, wherein one surface of the sheet is coated with a non-adhesive material selected from polyethylene glycol, polylactide or poly(DL-lactide-co-glycolide).

18. The tissue-adhesive sheet according to claim 10, wherein the matrix is made up from the following ingredients in the proportions indicated:
   a) terpolymer 20-80% w/w;
   b) additional synthetic polymer(s): 0-30% w/w;
   c) plasticiser(s): 0-30% w/w;
   d) aminated and/or thiolated polymer(s): 0-10% w/w; and
   e) non-adhesive film-forming polymer(s): 0-10% w/w.

19. A method for the manufacture of the tissue-adhesive sheet according to claim 10, which method comprises:
   dissolving or dispersing the one or more polymers in a suitable solvent;
   casting the resulting solution in a suitable mould or onto a suitable plate;
   drying the cast solution to remove the solvent; and
   curing to achieve cross-linking of the one or more polymers of the matrix, thereby forming the tissue-adhesive sheet.

* * * * *